United States Patent [19]

Tai et al.

[11]  4,061,695

[45]  Dec. 6, 1977

[54] PHOSPHATE ESTERS

[75] Inventors: Wun Ten Tai, Pallos Hills; Lawrence A. Mura, Homewood; Kenneth G. Phillips, River Forest; Edward G. Ballweber, Glenwood, all of Ill.

[73] Assignee: Nalco Chemical Company, Oak Brook, Ill.

[21] Appl. No.: 632,066

[22] Filed: Nov. 14, 1975

[51] Int. Cl.$^2$ .............................. C07F 9/09; C02B 5/06
[52] U.S. Cl. ....................................... 260/929; 252/80; 252/175; 260/978
[58] Field of Search ............... 260/920, 978, 928, 929, 260/920, 978

[56] References Cited

U.S. PATENT DOCUMENTS

| 3,413,380 | 11/1968 | Snyder | 260/920 |
| 3,639,533 | 2/1972 | De Pierri, Jr. | 260/978 X |

*Primary Examiner*—Anton H. Sutto
*Attorney, Agent, or Firm*—Hill, Gross, Simpson, Van Santen, Steadman, Chiara & Simpson

[57] ABSTRACT

Phosphate esters including polymers are produced by mixing polyols, such as glycerol, with phosphoric acid material followed by heating under reduced pressures in the presence of inorganic base to temperatures of from about 135° to 165° C. By maintaining reactants under subatmospheric conditions, water is removed as formed. The products have utility as scale suppressant additives to water used in heat exchange and cooling tower applications.

5 Claims, No Drawings

PHOSPHATE ESTERS

BACKGROUND OF THE INVENTION

Phosphate esters have heretofore been proposed for use in water as scale inhibitors. For example, Mickus et al U.S. Pat. No. 3,580,855 teaches addition of certain polyphosphoric acid reaction products with polyols at the rate of 5 to 1000 parts per million to water for creation of anti-corrosive, anti-scaling, anti-settling water systems. Apparently, others have also reported scale inhibition in water with similar reaction products.

In Mickus et al, reaction products of polyphosphoric acid with glycerol have previously been produced by heating the reactants together at about 70° to 110° C. for about 4 to 6 hours. Aqueous liquid phase conditions are employed, and water is allowed to accumulate as a byproduct during reaction. This prior art reaction characteristically goes only to about 10 to 25 percent completion (based on inorganic phosphoric acid starting materials). It is generally undesirable to raise the temperature of this reaction in hopes of shifting reaction equilibrium further to the right (towards greater conversion) because the polyol used can tend to degrade or decompose without forming desired products. Thus, glycerol dehydrates fairly easily to acrolein beginning at about 145° C., and higher molecular weight glycols are characteristically even more temperature sensitive as respects thermal degradation.

BRIEF SUMMARY OF THE INVENTION

There has now been discovered a process whereby polyols can be reacted with phosphoric acid materials relatively rapidly, simply, and if desired, substantially completely, so that, characteristically, at least about 90% conversion of starting materials can be obtained (based on inorganic phosphoric acid starting materials), and even substantially complete conversions of inorganic phosphate starting materials may be achieved. Thus, a novel and very useful process is provided wherein, a single process step, higher relative weight percentages of polyol phosphate reaction ester products are producable than heretofore achievable in this art by reaction between polyol and inorganic phosphate material. Such process also permits some regulation of the relative quantities of inorganic phosphates, polyols, and phosphate esters (including polymers) present in a given reaction product.

It has also been discovered that such process produces a new class of organophosphate ester compositions in which one class of components comprises organophosphate ester compounds and another class of components comprises polymeric organophosphate esters. Such compositions can be readily dissolved in water and the resulting solutions are surprisingly characteristically very water stable. Because of the complex nature of the chemistry involved, it is not now possible to identify the structural nature of all the individual various products produced by the process of this invention, as those skilled in this art will understand.

In one main aspect, this invention provides a new and improved process for making organo phosphate compounds with very high conversions of starting materials.

In another aspect, this invention provides a new class of organo phosphate compositions which are useful for scale inhibition in dilute aqueous systems.

Other and further aims, objects, purposes, advantages, uses, and the like for the present invention will be apparent to those skilled in the art from the present specification.

DETAILED DESCRIPTION

More particularly, the present invention is directed to a process for making organophosphate esters in high yield. The process involves as one step the simultaneous heating, removing of water, and maintenance of a reactant mixture in a region or zone of reaction under reduced pressure (relative to atmospheric) in the presence of inorganic base.

The reaction mixture includes two classes of components. One class of components in the reaction mixture comprises at least one phosphoric acid material selected from the group consisting of phosphoric acid and polyphosphoric acid. The other class of components in the reaction mixture comprises at least one polyol. Such polyol is characterized by a. having from 2 to 7 carbon atoms per molecule,
b. having from 2 to 4 hydroxyl groups per molecule distributed so that not more than one oxygen atom is substituted on each carbon atom in each molecule, and
c. being selected from the group consisting of hydroxyl substituted saturated aliphatic hydrocarbons.

The inorganic base comprises at least one material selected from the group consisting of alkali metal hydroxides (preferred), alkaline earth metal hydroxides, and ammonia (ammonium hydroxide) and such base is present in a minor amount relative to the total reaction mixture.

A preferred phosphoric acid material for use in this invention is phosphoric acid, and a presently more preferred such material is orthophosphoric acid. Preferred polyols are glycerol, ethylene glycol and pentaerythritol, and a presently more preferred polyol is glycerol.

An apreciable quantity of water can be initially present in a reaction zone, but the reaction conditions are such that this water, if present, is removed in an initial phase, after which the water present is removed from such zone substantially and preferably at a rate about equal to the rate at which water is generated in such zone by reason of the reaction occurring therein between the reactants (e.g. initially polyol and phoshoric acid material). Once any initially present excess water is removed, the total amount of water present in such zone during such heating is generally negligible, and preferably not more than about 5 weight percent of the total weight of said polyol and said phosphoric acid material present.

Process variables (broad ranges and more preferred ranges) are described in Table 1 below:

TABLE I

| PROCESS VARIABLES | | |
|---|---|---|
| Variable | Broad Range | Preferred Range |
| Zone temperature | 130–175° C | 135–165° C |
| Zone pressure | 50 mm | 0–400 mm |
| Mole ratio of polyol to phosphoric acid material (based on 100% phosphoric acid) | 0.5–1.5 | 0.56–0.77 |
| Mole ratio of inorganic base to total phosphoric acid material present in zone | 0.1–1.0 | 0.25–0.75 |
| Quantity of water initially present (based on the total amount percent | 0–50% | 0–20% |

TABLE I-continued
PROCESS VARIABLES

| Variable | Broad Range | Preferred Range |
|---|---|---|
| of phosphoric acid material used) | | |

The components of the reaction mixture can be charged to the reaction zone in any desirable manner as can the inorganic base. Conventional sources for the starting materials are suitable. The reaction zone can be any suitable reaction vessel, kettle, or the like, as those skilled in the art will appreciate. The process can be practiced batch-wise (presently preferred) or continuously.

The product of the reaction between polyol and phosphoric acid material is a composition which characteristically comprises (on a 100 weight percent total basis):

a. from about 0 to 20 weight percent total inorganic phosphate, and b. the balance up to 100 weight percent being organophosphate compounds which comprise reaction products of starting polyol with starting phosphoric acid material and which characteristically typically contain at least one phosphate ester group per molecule.

Since phosphoric acid materials and polyols each contain a plurality of potentially reactive hydroxyl groups, the reacting of one such polyfunctional type material with the other polyfunctional type material can characteristically produce dozens of reaction products. In general, the lower the percent of reaction completion, the lower the percentage of organic phosphate esters formed. Furthermore, with such polyfunctional type materials, the conditions employed for reaction can vastly alter the type of reaction or reactions which occur and the nature of the resulting products as well.

To analyze a given product produced by the practice of the process of this invention for its exact constituents is an extremely difficult problem, even with sophisticated tools, such as gas chromatography, nuclear magnetic resonance, mass spectography, and the like. Typically, those skilled in this art find it practical in normal practice to make routinely three primary determinations for a given reaction product: (1) free phosphoric acid; (2) total inorganic phosphate; and (3) total phosphate. Then, the total organic phosphate content is determined by the difference between total phosphate and total inorganic phosphate, since free phosphoric acid is already counted into total inorganic phosphate.

Thus, when such a reaction goes to the 15 to 25 percent completion as taught by Mickus et al in U.S. Pat. No. 3,580,855, it is found that the total organic phosphate produced is typically in the range of from about 15 to 25%, as when stoichiometric amounts of polyphosphoric acid are reacted with glycerol at temperatures ranging from about 70° to 110° C. However, when in accord with the present process teachings, a reaction is conducted in the presence of inorganic base, and water is removed during this reaction, the total organic phosphate produced is typically in the range above indicated for this same reaction using similar temperature ranges (see Table 1).

In the present invention's compositions, the amount of phosphate ester polymer present among the organophosphate compounds can range broadly from about 0.5 to 75 weight percent of the total amount of organophosphate compounds present but preferably from about 20 to 60 weight percent thereof. Such polymeric components have a molecular weight, for purposes of the present invention of at least about 500 with the upper molecular weight being such that the resulting polymer is water soluble. The typical upper molecular weight limit in any given composition of this invention can vary, depending upon variables such as starting materials employed and process conditions utilized, but a typical upper limit can be considered to be for illustration purposes around 1,600. For purposes of the present invention, molecular weights can be determined by gel permeation chromatography.

Composition variables (broad ranges and more preferred ranges) are described in Table 2 below.

TABLE 2
PRODUCT COMPOSITION CHARACTERISTICS

| | Broad Range | Preferred Range |
|---|---|---|
| Total Inorganic | 0–20 | 0–15 |
| Total Organophosphate | 80–100 | 85–100 |
| Phosphate ester polymer (based on total organophosphate) | 0.5–75 | 20–60 |

As produced, compositions as above described of this invention are typically at a temperature of from about 135° to 165° C as above indicated (see Table 1). The resulting product is then allowed to cool to a temperature ranging from 60° to 130° C, and preferably in the range of from about 100° to 110° C. When at this cooled temperature but still elevated, a composition is then admixed with sufficient water to produce an aqueous solution from about 5 to 70 percent (total solution basis) of a composition as above described, and more preferably from about 15 to 25 weight percent (same basis). If, instead of being dissolved in a water solution, the composition solidifies, it does not readily re-dissolve in water at a subsequent cooled temperature.

Products produced by this invention, due to low orthophosphoric acid contents, display scale inhibition activity. Since the prior art teaches that relatively high quantities of orthophosphoric acid, as produced by Mickus et al in U.S. Pat. No. 3580855, in a scale inhibited water solution tend to be detrimental for the reason that the calcium ions commonly present in water tend to form a calcium phosphate therewithin which tends to result in a precipitate and which tends to encourage deposition of material and scale build up on heat exchange surfaces (typically metal), such acid is preferably avoided in making products for scale inhibition usage. However, since phosphoric acid and polyphoshoric acid are known to function in water solution somewhat like a corrosion inhibitor, it is satisfactory to have some relatively small amount of such phosphoric acid materials present in a composition of this invention for scale inhibition usage. The small amount of any residual polyol present in a given product of this invention to be used for scale inhibition does not appear to have significance in this field of use.

In one preferred mode of practicing the present invention the reactants comprise glycerol and orthophosphoric acid with the total amount of water present being under about 20%, as indicated in Table 2. Alternatively, the polyol can be ethylene glycol. With these preferred starting materials, one employs process conditions, and achieves product compositions as briefly summarized below in Table 3.

TABLE 3

| | Moles NaOH/H₃PO₄ | Moles OPA(1)/ Polyol | Temp. (° C) | Press. (mm Hg) | Time (min.) | % org. PO₄(2) | Wt. OPA | % HMW(3) | Activity (M Alkalinity Limit |
|---|---|---|---|---|---|---|---|---|---|
| Glycerol | | | | | | | | | |
| Preferred | 0.25–0.75 | 1.3–1.8 | 135–165 | 50 | 90–120 | 88–94 | 6–12 | 20–60 | 400–425 |
| Maximum | 0.1 –1.0 | .65–2.0 | 130–175 | up to 400 | 30–400 | 83–95 | .5+17 | 0160 | 300–375 |
| Ethylene Glycerol | | | | | | | | | |
| Preferred | 0.5–2.0 | 1 | 150 | 150 | 330 | > 87 | 13 | 66 | > 325 |
| Maximum | 0.5–2.0 | 1–4 | 100–150 | 50–150 | 120–600 | 60 | not more than 15 | 25 | 300 |
| Pentaerythritol | | | | | | | | | |
| Preferred | 0.5–2.0 | 2.8 | 155–160 | 50 | 300 | 83 | not more than 15 | 80 | > 300 |
| Maximum | 0.5–2.0 | 1–8 | 100–155 | 20–50 | 200–600 | 60–90 | not more than 15 | 25 | > 300 |

TABLE 3 FOOTNOTES
(1)designates orthophosphoric acid
(2) designates organophosphate
(3)designates polymer with a molecular weight ranging from 500 to 1600

In the preferred practice of the present invention, the combination of starting materials comprising, for the phosphoric acid material, polyphosphoric acid, and for the polyol, pentaerythritol and/or glycerol, is to be avoided since experience has shown that this combination of starting materials reacts into undesirable organic end products from the standpoint of displaying good scale suppression properties in dilute water solutions. This circumstance actually points up a further advantage of the process of the present invention in respect to the ease with which orthophosphoric acid can be reacted with a polyol here because the presence of caustic with a phosphoric acid generates in situ orthophosphoric acid as a partial sodium salt in the course of the practice of the present invention and the products have excellent scale suppression properties.

Once one prepares a composition of this invention as described above and cools same, but before or at the time one mixes same with water, it is preferred to have excess caustic present in order to maintain the identity of the high molecular weight phosphoric acid species.

The requisite amount of inorganic base for a preferred mode of practicing the process of this invention as shown in Table 1 is charged along with the phosphoric acid. If one does not have the base at the start of the reaction, when one finishes the reaction, and one dissolves the reaction product into water, one characteristically does not contain a final product which contains more than about 82% organic phosphate, whereas, with base included initially, the amount of inorganic phosphate present in a product composition can be reduced to the desired level indicated above in Table 2.

The above-indicated preferred rates of addition for inorganic base promote the production of high molecular weight polymeric material in the polymer portion of compositions of the present invention. Characteristically, a natural upper limit upon the maximum useful quantity of inorganic base which can be present in a reaction zone during the course of practicing the process of the present invention tends to exist because the reaction mass displays an increase in viscosity with increasing amounts of added inorganic base so that with increasing amounts of added base, a point is reached at which the reaction mass becomes so viscous that stirring and agitation thereof becomes very difficult and removal of the reaction mass from the reaction zone becomes difficult, if not impossible, owing to viscosity levels which impede flow. The level at which the viscosity thus becomes excessive is somewhat variable depending upon the starting materials and process conditions employed, but a useful upper limit is shown in Table I (see broad range for inorganic base addition).

In general, a composition of the present invention as manufactured and while still in a fluid form before solidification upon cooling can be dispersed in a polar solvent which allows solubility of the product.

When a composition of the present invention containing an amount of inorganic base, as indicated above in the Tables, is dissolved in water, there results a solution which characteristically has a pH under about 4. Characteristically, the product solution upon storage (standing) displays a tendency to experience degradation of the polymeric fraction so that the total quantity of polymeric phosphate ester present in a given product solution appears to decline with time. Typical half-lifes (that is, the time when the quantity of polymeric material present in a product solution has changed to approximately one-half of its initial value upon standing at room temperatures and pressures) are not known with certainty at this time, but are believed to be typically in the rane of from about 300 to 1000 hr for solutions wherein the weight percentage of water present (based on total solution weight) falls in the range of from about 30 to 95 with the balance thereof being composition of this invention.

In accordance with the teachings of the present invention, it has been discovered that surprisingly and unexpectedly, it is possible to stabilize the polymeric fraction of a composition of this invention against such deterioration on storage by incorporating into a product aqueous solution an additional quantity of inorganic base. For such a stabilization, the quantity of inorganic base added to a starting product solution of this invention is such as to bring the pH of such solution into a range of from about 4 to 10, and more preferably in the range of from about 4 to 7. For such stabilization purposes, a presently preferred inorganic base is an alkali metal hydroxide, more preferably, sodium hydroxide. After such stabilization, the half-life of the polymeric fraction of a composition of this invention when an aqueous solution appears to be indefinitely suspended, though some deterioration thereof may occur with time (the extent of which is presently unknown).

In practicing the process of the present invention, it is generally preferred during an initial heating of the reactants to bring same to a temperature within the ranges indicated above in Table I in as brief a time as practical, and it is also preferred, once the reactant mixture has achieved a desired conversion of starting materials to organo phosphate products, to cease heating and to commence cooling of the reaction mass, generally for the reason that the yield of organo phosphate is apparently somewhat improved. Prolonged heating of a reaction mass after a desired degree of conversion has been achieved also may contribute possibly to the degradation of polyolester products.

Pressures greater than those indicated above in Table I can tend to be detrimental to the reaction and to reduce the total conversion of starting materials to organo phosphate products.

In the case of a process sequence of the present invention practiced with orthophosphoric acid (such as about 1 mol) and with glycerol (such as about 1 mol), conversions of about 81% even at a low pressure of about 10mm Hg appear to be characteristic because of the decomposition of glycerol to acrolein, and, possibly, of glycerol phosphate products to orthophosphoric acid and acrolein based phosphates at temperatures above about 145° C. However, such decompositions are acid catalyzed and appear to be suppressible by the addition of caustic to the reaction system in accordance with the teachings of the present invention. When a sufficient amount of caustic is added, such as about 1 mol of sodium hydroxide to 1 mol of $H_3PO_4$ in the system being exemplified here, hardly any decomposition is detected (very little acrolein liberation and white colorless product is produced) and the conversion is high (98%) for an equal molar reaction of phosphoric acid with glycerol at temperatures in the range of from about 174° to 183° C and at pressures of about 50mm Hg.

While sodium hydroxide, for an example of one base, improves the conversion of, for example, a mixture of glycerol and orthophosphoric acid to phosphate esters, the use of sodium hydroxide in such a reaction increases the solution viscosity, as indicated above, to such an extent that the reaction mass is generally immobile at about 165° C. at 50mm Hg pressure. The use of a reduced amount of sodium hydroxide is therefore necessary in order to provide a stirable reaction system in this instance.

By employing the combination of vacuum distillation and presence of inorganic base in accordance with the practice of the process of this invention, polyphosphoric acid can be reacted with polyol to obtain high conversion, e.g., typically in excess of about 90 weight percent in the case of polyphosphoric acid and glycerol in molar proportions.

In general, the lower pressures employed in the practice of this invention (relative to atmospheric pressures) favor higher conversions. Also, in general, higher reaction temperatures tend to shorten reaction times and also to permit the use of lower pressures (relative to atmospheric). However, higher temperatures generally suggest the desirability of using appropriate heating devices in plant scale reactors which can sometimes be disadvantageous from an equipment availability standpoint. Also, particularly in plant scale operations, decomposition may be encountered at higher temperatures than say about 165° C. when a glycerol polyol starting material is employed and the sodium hydroxide is employed at a relatively small amount within the ranges above indicated in order to provide good stirability characteristics. In general, conversions at lower reaction temperature are lower even if prolonged heating times are involved. It appears, and there is no intent to be bound herein by theory, that a certain energy barrier may have to be overcome in order to achieve a desired level of esterification such as is associated with the high conversions achieved by the practice of the present invention.

In general, at a given reaction condition in a reaction zone, when a maximum level of conversion is reached, it appears that it cannot be further improved by prolonged heating of the reaction mass. Furthermore, a prolonged heating of the reaction mass at an elevated temperature quite often can be reflected in small decreases in the level of conversion initially achieved. In general, reaction times of less than two hours are found to be satisfactory at temperatures in the range of from about 145° to 165° and 50mm Hg pressure when reacting a phosphoric acid material such as orthophosphoric acid with a polyol material such as glycerol.

As indicated, a base such as sodium hydroxide tends to increase the viscosity of a reaction system and hence decrease its stirability. A mol ratio of sodium hydroxide to polyphosphoric acid of about 2 results in poor stirability at about 165° C. when the mol ratio of glycerol to polyphosphoric acid is 3 or less. The increased amount of glycerol improves the stirability by functioning as a diluent, apparently, and when the amount of glycerol is increased to a glycerol/polyphosphoric acid mol ratio of about 4, the reaction system is stirable even at a sodium hydroxide to polyphosphoric acid mol ratio of about 3.

When the amount of sodium hydroxide employed is such as to produce a mol ratio of sodium hydroxide to polyphosphoric acid of about 1, the decomposition is sufficiently suppressed to give a desired conversion and good stirability at temperatures in the range of from about 135° to 165° C. for the range of polyols to polyphosphoric acid mol ratios preferred in the practice of the present invention.

In general, higher glycerol/polyphosphoric acid mol ratios favor higher conversions. The improvement is generally substantial. By increasing the glycerol/polyphosphoric acid mol ratios from about 2.2 to 4.0, the conversions are increased typically by values ranging from about 87 to 97 weight percent (based on initial phosphoric acid charged).

The lower limit for the glycerol/polyphosphoric acid mol ratios needed to achieve a desired conversion of greater than about 85 weight percent based on phosphoric acid is about 2.2. At a glycerol/polyphosphoric acid mol ratio of 2.0, a conversion is only about 81 weight percent (same basis). Because of the inherently greater thermal stability, in general, it appears that ethylene oxide condensates with glycerol may give slightly better conversions than glycerol under substantially identical reaction conditions.

Since polyphosphoric acid is currently less expensive than polyol materials, conversions being equal, the raw material costs of polyolesters are lower when less quantities of polyols are employed in a given reaction.

In a preferred mode of practicing this invention in order to achieve conversions of at least about 85 weight percent, vacuum pressures of at least about 50mm Hg appear to be desirable. A substitution of, for example, an 85 weight percent orthophosphoric acid material for a 115 weight percent polyphosphoric acid (phosphoric acid) has no affect on the final conversion in a product composition. Such a substitution can eliminate handling problems associated with 115 weight percent phosphoric acid (polyphosphoric acid). Similarly, natural glycerin (86 to 88 weight percent glycerin) can be substituted for synthetic glycerin (99.5% glycerin) with no loss in conversion or activity.

In an glycerine/orthophosphoric acid reaction system studied (2.58 mol $H_3PO_4$, 1.68 mole glycerine and a total of 2.1 mole Na OH based on $H_3PO_4$), the effect of the amount of Na OH added before esterification is to increase the amount of high molecular weight material (polymeric) produced, and to incresase the conversion of esters when about ½ of the Na OH (about 1 mol) is added before the esterification is started. When about ⅓ to ⅔ of the total caustic is added before esterification, conversions are excellent and greater than about 55 weight percent of the product is polymeric material having a molecular weight greater than about 500. When greater or lesser amounts of Na OH are added at first, conversions and the amount of such polymeric material produced both decrease. See Table V below and the examples.

In this process the presence of caustic converts both phosphoric acid and polyphosphoric acids into the partial sodium salt of orthophosphoric acid. In a similar respect, phosphorous pentoxide is converted to the partial sodium salt of orthophosphoric acid. Phosphate analyses of the above reaction mixtures have shown both that during water removal 25 percent of the inorganic phosphate is converted to polymeric phosphate and that the amount of polymeric inorganic phosphates formed is independent of the original phosphate source.

EMBODIMENTS

The present invention is further illustrated by reference to the following examples. Those skilled in the art will appreciate that other and further embodiments are obvious and within the spirit and scope of this invention from the teachings of these present examples taken with the accompanying specification.

EXAMPLE 1

392 grams of orthophosphoric acid and 220.8 grams of 50% sodium hyroxide are charged to this mixture. The total amount of water present is initially about 5.8 weight percent of the total charge.

After 30 minutes of heating to 147° C, the pressure in the interior of the vessel is reduced to, and continuously maintained at, about 50mm Hg, and the starting mixture is maintained at the temperature of about 147° C for 90 minutes and then the temperature is increased to 155° C for 8 minutes. Water vapor is removed continuously from the vessel interior.

Thereafter, the heating is ceased and the vessel internal pressure is allowed to return to atmospheric. The vessels contents are cooled to about 90° C before depressurization.

The reaction product is found to comprise on a 100 weight percent total phosphate weight basis about 12.1 weight percent inorganic phosphate and about 87.9 weight percent organic phosphate. The weight percent of polymeric material present based on total organophosphate content of the product, such polymeric material having a molecular weight greater than 500 was about 40%.

The amount of total phosphate and inorganic phosphate present was determined photometrically. The amount of organic phosphate present in the product was then determined by difference. The product was separated into its molecular weight components by Gel Permeation Chromotography and displayed by a strip chart recorder. The amount of polymer material having a molecular weight greater than 500 was determined by area integration.

EXAMPLE 2

The reaction product of Example 1 (which is initially at a temperature of about 90° C) is slowly added to deionized water (which is itself initially at ambient temperatures) with stirring. The composition from Example 1 dissolves in the water to form a solution. The product solution contains about 47.9 weight percent water with the balance up to 100 weight percent being the composition as prepared in Example 1. This product solution contains approximately 32 wt. % total phosphate. When this composition is then cooled to room temperature and stored for a period in excess of about 4 months, it is found that the fraction thereof which is polymeric and which has a molecular weight in excess of about 500 (determined as in Example 1) has been reduced to a value in the range of from about 40 to 12 weight percent. The total amount of dissolved inorganic phosphate apparently remains substantially constant after this storage. The product solution has a pH of about 2.1.

EXAMPLE 3

The reaction product of Example 1 is dissolved in the manner of Example 2 in an aqueous solution having previously dissolved therein sufficient sodium hydroxide to make the pH of the product solution fall in various ranges as tabularized below in Table 4. When the resulting solutions are then stored under accelerated aging conditions it is found that the polymer fraction in the pH 4 and pH 8 solutions have been changed during the storage period only slightly while the polymer fraction in the pH 2 solution has been significantly reduced. It is therefore, concluded that addition of inorganic base to the water or the solvent acts as a stabilizer in maintaining the high molecular weight fraction of the composition of Example 1.

TABLE 4

| Product | HMW[1] 0 Days Aging | HMW 7 Days Aging (120° F) | HMW 28 Days Aging (120° F) |
|---|---|---|---|
| 2.1 | 46.6 | 31.4 | 18.1 |
| 4.1 | 45.0 | 46.8 | 41.5 |
| 8.0 | 52.6 | 52.1 | 51.4 |
| 11.1 | 50.0 | 34.5 | 30.0 |

[1]Weight percent of polymeric material present based on total organophosphate content of the products, such polymeric material having a molecular weight greater than 500.

EXAMPLE 4

The reaction product of Example 1 is cooled to room temperatures and is found to form a hygroscopic tacky dark brown solid which dissolves slowly in water and in organic solvents such as glycerol.

EXAMPLE 5

The procedure of Example 1 is repeated, except that here an ethoxylated glycerol is used in place of glycerol. The ethoxylated glycerol is formed by condensing 2 to 3 moles of ethylene oxide with glycerol. The mole ratio of the ethoxylated glycerol to sodium hydroxide is 3.86, while the mole ratio of sodium hydroxide to phosphoric acid is 0.52.

The initial heating at atmospheric pressure was 180° C for 1 hour after which the pressure was reduced to 50mm at this same temperature. These conditions were monitored for one hour and the reaction was terminted.

The reaction product is cooled from 168° C to 106° C, while still at 50mm pressure, and then depressurized.

The reaction product is found to comprise on a 100 weight percent total phosphate weight basis about 9 weight percent inorganic phosphate and about 91 weight percent organic phosphate.

EXAMPLE 6

The laboratory reactor used is a 500 ml resin flask equipped with a mechanical stirrer, thermometer, two addition funnels, and a still head connected to a water-cooled condenser, receiver, and a vacuum line. Since small quantities of acrolein are liberated during the reaction, a bisulfite trap is necessity for any large scale preparations.

| Mole Ratio $H_3PO_4$ : glycerine — 1.54 | |
|---|---|
| Raw Materials | Weight % Charge |
| 85% $H_3PO_4$ | 36.27 |
| 99.5% glycerine | 18.86 |
| 1st 50% NaOH solution | 7.51 |
| soft $H_2O$ | 24.39 |
| 2nd 50% NaOH solution | 12.97 |
| Dow Corning 544 anti-foam | use as needed |
| | 100.00 |

The 85% phosphoric acid is charged into the reactor. The agitator is started, and the first 50% NaOH addition is begun. During the addition the temperature rises to 100°–125° C. After the addition is completed the pressure is reduced to 50 mm, and the partially neutralized phosphoric acid is heated to 155° C. The solution is held at 155° C at 50 mm until the overhead ceases. With full heating on the glycerine is added over a 2 hour period. As the glycerine is added the pot temperature will gradually decrease and level off at about 135° C. After the glycerine addition is completed the reaction is heated back to 155° C and held at this temperature at a pressure of 50 mm until the overhead stops. During this period neat anti-foam is added as needed to the reaction. After the overhead has stopped, the pot is cooled to 140° C, and the vacuum is released with nitrogen. When the temperature falls to below 115° C, the soft water is added. The solution is cooled to 50° or 60° C, and the second portion of 50% NaOH is added to such a rate so that the temperature remains below 75° C. The reaction is cooled to ambient temperature, and the product is discharged into lined drums. The average laboratory conversion based on the amount of phosphoric acid converted into organic phosphate is 88%. The fraction thereof which is polymeric and which has a molecular weight in excess of about 500 (determined as in Example 1) was found to be about 55%.

EXAMPLES 7 AND 8

Two pilot plant reactions (one with natural glycerine-(86% glycerine) and the other with synthetic glycerine -(99.5%) were conducted in a 750 gallon stainless steel reactor. Both reactants gave 86% conversion to organic phosphate. The product from the pilot plant reactions have a pH of about 2.1, a Brookfield viscosity of 200 cps, contain approximately 32 wt. % total phosphate, and the fraction thereof which is polymeric and which has a molecular weight in excess of about 500 (determined as in Example 1) was found to be about 400%.

EXAMPLE 9

The procedure of Example 6 is repeated with the following variables:

| Mole Ratio $H_3PO_4$ : glycerine — 1.32 | |
|---|---|
| Raw Materials | Weight % Charge |
| 85% $H_3PO_4$ | 35.17 |
| 99.5% glycerine | 21.32 |
| 1st 50% NaOH | 7.28 |
| soft $H_2O$ | 23.65 |
| 2nd 50% NaOH | 12.58 |
| Dow Corning 544 anti-foam | use as needed |
| | 100.00 |

The reaction procedure is identical to Example 7. Two laboratory reactions gave a conversion of 94% while a pilot plant reaction in the 750 gallon stainless steel reactor gave a conversion of 88%. The pilot plant product has a pH of 2.0, a Brookfield of 200 cps, and contains approximately 35 wt. % total phosphate, and the fraction thereof which is polymeric and which has a molecular weight in excess of about 500 (determined as in Example 1) was found to be about 400%.

EXAMPLE 10

Into a 1 liter resin flask equipped with a mechanical stirrer, thermometer, solids addition tube and distillation head are charged 323 grams 85% $H_3PO_4$. Then 66.7 grams of 50% NaOH is added slowly. The reaction flask is then evacuated to 50 mmHg, and heated to 155° C for 1 hour. 136g of pentaerythritol are then introduced in several portions while maintaining temperature at about 150° C to 50 mmHg. This mixture is held at 155°–160° C and 50 mmHg for about 4 hours, by which time the distillation of $H_2O$ had practically ceased and the amount of orthophosphoric acid remaining is 11.7% based on starting phosphoric acid. The reaction mixture is cooled to 110° C and 220g of deionized water is added with stirring. When all the product had dissolved in the $H_2O$, the solution is cooled and maintained at 50° C while 115g of 50% NaOH is added. The resulting product solution has a pH of 2.4 and contains 80% of polymeric material with molecular weight in excess of about 500 (determined as in Example 1).

EXAMPLE 11

Into a 1 liter reaction flask equipped with a mechanical stirrer, thermometer, addition funnel and distillation head with condenser was charged 230.6g of 85% $H_3PO_4$. To the acid, 48g of 50% NaOH is added slowly. The system is evacuated to 50 mm, heated to 150° C and held at the temperature for 1 hour. The pressure was then reduced to 150 mm and 124g of ethylene glycol is added over a period of 10 minutes. The reaction was held at 150° C and 150 mm for 4.5 hours then cooled to 120° C and 150g of deionized water added. After the product has dissolved, 83.0g of additional 50% NaOH is added, maintaining the temperature at 50° C during this addition. The product solution contained 10.3% of orthophosphate and 65.9% of polymeric material having a molecular weight of at least about 500.

In Table 5 one can see the effect of the amount of NaOH added before esterification on the amount of polymeric phosphate produced.

TABLE 5

| Reaction Number | (1) | (2) | (3) |
|---|---|---|---|
| 1 | 0.0 | 17.9 | 23.0 |
| 2 | 12.2 | 13.8 | 42.7 |
| 3 | 24.5 | 15.5 | 44.9 |
| 4 | 36.7 | 10.1 | 56.2 |
| 5 | 50.0 | 10.1 | 66.4 |
| 6 | 66.7 | 8.0 | 56.3 |
| 7 | 100.0 | 9.8 | 41.1 |

(1) Weight percent of the total amount of caustic in the final product which was charged before esterification. (Remaining caustic was added after completion of the reaction).
(2) Total weight percent of orthophosphate present in product.
(3) Weight percent of polymeric material present based on total organophosphate content of a product, such polymeric material having a molecular weight greater than 500.

EXAMPLE 12

Compositions of this invention are evaluated for $CaCO_3$ stabilization and in an Evaporative Heat Exchange Unit and the results obtained in terms of scale suppression activity are expressed as "M" alkalinity at break point or milligram deposits on tube walls in the apparatus.

In general, lower polyols/polyphosphoric acid mole ratios give more active products although the slope of the activity curve may level off somewhat after a mole ratio of about 3 is reached in this system.

The glycerol phosphate of Example 2 was added to the recirculating water of a pilot cooling tower system. This system consists of a recirculating water system which removes heat from a tube-shell heat exchanger. This heat is rejected in an induced draft cooling tower by means of evaporation of a small portion of the recirculating water. During the evaporation process the naturally occurring salts in the make-up water are concentrated until a chemically unstable condition is reached. At this condition calcium carbonate precipitates from the water and causes harmful deposition throughout the system. The glycerol phosphate mentioned above is added at concentrations from 5 to 20 ppm active. The addition of this material increases the concentrations obtainable in the recirculating water without harmful precipitation.

Example: The standard make-up water used is Chicago tap water which contains calcium (as $CaCO_3$) = 90 ppm, M total alkalinity (as $CaCO_3$) = 110 ppm. This water will concentrate to an M level of 170 ppm if no treatment is used. The addition of 20 ppm of the glycerol phosphate will allow concentrations of M alkalinity up to 400 ppm. This represents substantial savings in water.

The claims are:

1. An organophosphate composition comprising on a 100 weight percent total weight basis
   a. from about 5 to 70 weight percent water, and
   b. the balance up to 100 weight percent thereof being a phosphate ester composition,
   c. said phosphate ester composition comprising on a 100 weight percent total weight basis
      1. from 0 to about 15 weight percent inorganic phosphate,
      2. the balance up to 100 weight percent of any given said phosphate ester composition being organophosphate material, and
      3. said organophosphate material containing on a 100 weight percent total organophosphate weight basis from about 20 to 60 weight percent of polymeric material, said composition having been produced by the steps of
   A. simultaneously
      1. heating in a reaction zone at a temperature of from about 130° to 175° C at least one phosphoric acid material selected from the group consisting of phosphoric acid and polyphosphoric acid in admixture with at least one polyol which is characterized by
         a. having from 2 to 7 carbon atoms per molecule,
         b. having from 2 to 4 hydroxyl groups per molecule distributed so that not more than one oxygen atom is substituted on each carbon atom per molecule, and
         c. being selected from the group consisting of hydroxyl substituted saturated aliphatic hydrocarbons,
      in the presence of a minor amount of at least one inorganic base selected from the group consisting of alkali metal hydroxides, alkaline earth metal hydroxides, and ammonia, the mole ratio of said polyol to said phosphoric acid material as charged to said zone ranging from about 0.5 to 1.5, and the mole ratio of said inorganic base to said phosphoric acid material being from about 0.1 to 1.0,
      2. maintaining said reaction zone at a subatmospheric pressure, ranging from greater than 0 to about 400 mm Hg., and
      3. removing water from said zone at a rate at least about equal to the rate water generated in said reaction zone;
   B. cooling the resulting reaction product to a temperature in the range of from about 60° to 130° C; and
   C. admixing the so-cooled reaction product with and dissolving same in sufficient water to form a product solution comprised on a 100 weight percent total weight basis from about 5 to 70 weight percent water.

2. The organophosphate composition of claim 1 further containing sufficient added inorganic base dissolved in said water to produce a product solution having a pH ranging from about 4 to 10.

3. The organophosphate composition of claim 1 wherein said a phosphoric acid material is phosphoric acid.

4. The composition of claim 1 wherein said organophosphate polymeric material has a molecular weight of at least about 500.

5. A phosphate ester composition comprising on a 100 weight percent total weight basis
   A. from about 0 to 15 weight percent inorganic phosphate,
   B. the balance up to 100 weight percent of any given said composition being organophosphate material, and
   C. said organophosphate material containing on a 100 weight percent total organophosphate weight basis from about 20 to 60 weight percent of polymeric material, said composition having been produced by the process of simultaneously
   A. heating in a reaction zone at a temperature of from about 130° to 175° C at least one phosphoric acid material selected from the group consisting of phosphoric acid and polyphosphoric acid in admixture with at least one polyol which is characterized by
      1. having from 2 to 7 carbon atoms per molecule, 2. having from 2 to 4 hydroxyl groups per molecule distributed so that not more than one oxygen atom is substituted on each carbon atom per molecule, and
3. being selected from the group consisting of hydroxyl substituted saturated aliphatic hydrocarbons, in the presence of a minor amount of at least one inorganic base selected from the group consisting of alkali metal hydroxides, alkaline earth metal hydroxides, and ammonia, the mole ratio of said polyol to said phosphoric acid material as charged to said zone ranging from about 0.5 to 1.5, and the mole ratio of said inorganic base to said phosphoric acid material being from 0.1 to 1.0, B. maintaining said reaction zone at a subatmospheric pressure, ranging from greater than 0 to about 400 mm Hg, and C. removing water from said zone at a rate at least about equal to the rate water generated in said reaction zone.

* * * * *